(12) United States Patent
Ainger et al.

(10) Patent No.: US 11,376,209 B2
(45) Date of Patent: *Jul. 5, 2022

(54) ANTIDANDRUFF COMPOSITION AND METHOD OF USE

(71) Applicant: Conopco, Inc., Englewood Cliffs, NJ (US)

(72) Inventors: Nicholas John Ainger, Wirral (GB); Joanna Susan Dawson, Wirral (GB); Wei Gao, Fort Washington, PA (US); Adam Peter Jarvis, Liverpool (GB); Kinjalbahen Joshi, Collegeville, PA (US); Curtis Schwartz, Ambler, PA (US); Neil Scott Shaw, Warrington (GB); Inna Shulman, Langhorne, MI (US); Pierre Starck, Chester (GB); Sally Elizabeth Wood, Warrington (GB); Fanwen Zeng, Audubon, PA (US)

(73) Assignee: Conopco, Inc., Englewood Cliffs, NJ (US)

( * ) Notice: Subject to any disclaimer, the term of this patent is extended or adjusted under 35 U.S.C. 154(b) by 200 days.

This patent is subject to a terminal disclaimer.

(21) Appl. No.: 16/760,343

(22) PCT Filed: Oct. 19, 2018

(86) PCT No.: PCT/EP2018/078741
§ 371 (c)(1),
(2) Date: Apr. 29, 2020

(87) PCT Pub. No.: WO2019/086274
PCT Pub. Date: May 9, 2019

(65) Prior Publication Data
US 2021/0196614 A1 Jul. 1, 2021

Related U.S. Application Data

(60) Provisional application No. 62/581,132, filed on Nov. 3, 2017.

(30) Foreign Application Priority Data

Feb. 7, 2018 (EP) .................... 18155492

(51) Int. Cl.
*A61Q 5/02* (2006.01)
*A61K 8/81* (2006.01)
(Continued)

(52) U.S. Cl.
CPC ............ *A61K 8/8158* (2013.01); *A61K 8/044* (2013.01); *A61K 8/37* (2013.01); *A61K 8/44* (2013.01);
(Continued)

(58) Field of Classification Search
None
See application file for complete search history.

(56) References Cited

U.S. PATENT DOCUMENTS

| 4,298,494 A | 3/1981 | Parslow |
| 5,154,847 A | 10/1992 | LaPetina et al. |

(Continued)

FOREIGN PATENT DOCUMENTS

| EP | 0896027 | 2/1999 |
| EP | 0995791 | 4/2000 |

(Continued)

OTHER PUBLICATIONS

Search Report and Written Opinion in EP18155491; dated Jun. 28, 2018.

(Continued)

*Primary Examiner* — Jyothsna A Venkat
(74) *Attorney, Agent, or Firm* — Foley & Lardner LLP

(57) ABSTRACT

An aqueous anti-dandruff shampoo composition which comprises: (I) a cleansing surfactant selected from the group consisting of anionic surfactant, zwitterionic or amphoteric surfactant and nonionic surfactant; (II) suspended particles of an anti-dandruff agent, (III) an anti-settling, thickening polymer, wherein the anti-settling, thickening polymer, comprises: (a) 40 to 74.5 wt % of structural units of $C_{1-4}$ alkyl acrylate; (b) 20 to 50 wt % of structural units of methacrylic acid; (c) 0.2 to <5 wt % of structural units of 2-acrylamido-2-methylpropane sulfonic acid (AMPS); (d) 5 to 25 wt % of structural units of a specialized associated monomer having the following structure wherein $R^1$ is a linear saturated $C_{10-24}$ alkyl group; wherein $R^2$ is a hydrogen or a methyl group (preferably, wherein $R^2$ is a methyl group); and wherein n is an average of 20 to 28; with the proviso that the structural units of the specialized associated monomer (d) are derived from one of (i) a single specialized associated monomer (preferably, a single specialized associated monomer wherein $R^1$ is selected from the group consisting of a linear saturated $C_{12}$ alkyl group, a linear saturated $C_{18}$ alkyl group and a linear saturated $C_{22}$ alkyl group; more preferably, a single specialized associated monomer wherein R 1 is selected from the group consisting of a linear saturated C12 alkyl group and a linear saturated C18 alkyl group); (ii) two specialized associated monomers, wherein $R^1$ is, respectively, a linear saturated $C_{12}$ and a linear saturated $C_{18}$ alkyl group; or (iii) two specialized associated monomers, wherein $R^1$ is, respectively, a linear saturated $C_{18}$ alkyl group and a linear saturated $C_{22}$ alkyl group; (e) 0 to 1 wt % of structural units of acrylic acid; and (f) 0 to 2 wt % of structural units of multi-ethylenically unsaturated crosslinking monomer or chain transfer agent; and wherein the sum of the weight percentages of structural units (a)-(f) is equal to 100 wt % of the anti-settling, thickening polymer; and the use of such a composition in a method of treating hair or scalp.

(Continued)

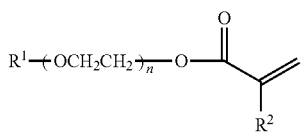

7 Claims, No Drawings

(51) Int. Cl.
- A61K 8/04 (2006.01)
- A61K 8/37 (2006.01)
- A61K 8/44 (2006.01)
- A61K 8/46 (2006.01)
- A61K 8/891 (2006.01)
- A61Q 5/00 (2006.01)
- A61Q 5/12 (2006.01)

(52) U.S. Cl.
CPC ............ *A61K 8/463* (2013.01); *A61K 8/8194* (2013.01); *A61K 8/891* (2013.01); *A61Q 5/006* (2013.01); *A61Q 5/02* (2013.01); *A61Q 5/12* (2013.01); *A61K 2800/48* (2013.01); *A61K 2800/5422* (2013.01); *A61K 2800/5428* (2013.01)

(56) References Cited

U.S. PATENT DOCUMENTS

| | | |
|---|---|---|
| 5,543,074 A | 6/1996 | Hague |
| 5,977,039 A | 2/1999 | Gordon et al. |
| 6,001,344 A | 12/1999 | Villa |
| 6,063,857 A | 5/2000 | Greenblatt et al. |
| 6,106,816 A | 8/2000 | Hitchen |
| 6,906,016 B1 | 6/2005 | Tsaur |
| 7,541,320 B2 | 2/2009 | Dabkowski |
| 8,642,056 B2 | 2/2014 | Souzy et al. |
| 2003/0108503 A1 | 6/2003 | Maubru et al. |
| 2010/0009891 A1 | 1/2010 | Canto et al. |
| 2014/0112966 A1 | 4/2014 | Souzy et al. |
| 2014/0178325 A1 | 6/2014 | Martinez-Castro et al. |
| 2014/0336101 A1 | 11/2014 | Mertens |
| 2017/0027846 A1 | 2/2017 | Souzy et al. |
| 2017/0037170 A1* | 2/2017 | Gonzalez ................. A61Q 5/12 |

FOREIGN PATENT DOCUMENTS

| | | |
|---|---|---|
| EP | 2853570 | 4/2015 |
| EP | 2933280 | 10/2015 |
| WO | WO9113145 | 9/1991 |
| WO | WO2012120330 | 9/2012 |
| WO | WO2016100466 | 6/2016 |
| WO | WO2017042004 | 3/2017 |
| WO | WO2017200786 | 11/2017 |

OTHER PUBLICATIONS

Search Report and Written Opinion in EP18155492; dated Jul. 4, 2018.
Search Report and Written Opinion in EP18155489; dated Jul. 4, 2018.
Search Report and Written Opinion in EP18155490; dated Jul. 3, 2018.
Search Report and Written Opinion in PCTEP2018078742; dated Nov. 22, 2018.
Search Report and Written Opinion in PCTEP2018078741; dated Nov. 22, 2018.
Search Report and Written Opinion in PCTEP2018078743; dated Dec. 3, 2018.
Search Report and Written Opinion in PCTEP2018078740; dated Dec. 14, 2018.
Search Report and Written Opinion in EP19151019; dated May 17, 2019.
Robert Y Lochhead et al.; A Review of Recent Advances in the Polymeric Delivery of Attributes in Cosmetics and Personal Care Products; Polymeric Delivery of Therpeatics; Jan. 1, 2010; 1-20 (also as XP055586489).
Search Report and Written Opinion in PCTEP2019086872; dated Feb. 27, 2020.

* cited by examiner

ANTIDANDRUFF COMPOSITION AND METHOD OF USE

CROSS REFERENCE TO RELATED APPLICATION

This application is a U.S. National Stage Application under 35 U.S.C. § 371 of International Application No. PCT/EP2018/078741, filed on Oct. 19, 2018, which claims the benefit of European Application No. 18155492.4, filed on Feb. 7, 2018 and U.S. Provisional Application No. 62/581,132 filed on Nov. 3, 2017, the entire disclosures of which are hereby incorporated by reference for any and all purposes.

FIELD OF THE INVENTION

The present invention relates to antidandruff shampoo compositions, containing an insoluble antidandruff agent and an anti-settling thickening polymer, for use in the treatment of hair and/or scalp. The invention also relates to the use of these compositions for the treatment of inflammatory skin conditions such as scalp itch and dandruff. The invention further relates to the use of such a composition in a method of treating hair or scalp.

BACKGROUND AND PRIOR ART

Aqueous compositions having insoluble ingredients suspended therein have desirability for a variety of conventional uses, such as in the home care and personal care areas. One such composition is an antidandruff treatment, for application to the scalp and hair, where a benefit agent such as an antidandruff active or a silicone is typically suspended within an aqueous base. During use, the benefit agent is desirably deposited onto the scalp or hair.

To be acceptable to consumers, such aqueous compositions desirably exhibit both an appealing look and feel, both in the pack and during use, for example product dispensing, spreadability, smooth feel and so on. This, however, in complex aqueous formulations containing suspended insoluble ingredients, presents significant challenges.

Indeed, the incorporation of anti-dandruff ingredients suspended in aqueous anti-dandruff shampoo compositions, creates a variety of complications. For example, certain insoluble anti-dandruff ingredients have a density disparate from the continuous phase of the composition. This density mismatch can lead to compositional instability. In systems containing insoluble materials with a density less than that of the continuous phase, the insoluble materials tend to float to the top surface of the continuous phase (i.e., creaming). In systems containing insoluble materials with a density greater than that of the continuous phase, the insoluble materials tend to sink to the bottom of the continuous phase (i.e., settling).

Suspended insoluble antidandruff particles have a tendency to aggregate in aqueous cosmetic products thus decreasing its available surface area with a consequential loss of antidandruff activity.

Further, effective deposition of suspended agents can be problematic, especially from rinse off cleansing compositions, which are designed to remove substances such as dirt and oils from surfaces and wash them away. Thus, getting enough agent onto the surface, in order to give a big enough beneficial effect, is difficult to achieve.

Furthermore, it is desirable that anti-dandruff ingredients are deposited in a way that does not significantly impact their bioavailability on the scalp surface (that is to say the dissolution and/or diffusion of the ingredients on the scalp surface is not overly reduced).

Structurants have traditionally been incorporated into shampoos to adjust viscosity, maintain phase stability (i.e. preventing creaming and settling of suspended agents). Structurants also have the ability to control the aggregation of suspended insoluble ingredients by preventing their approach and subsequent adhesion.

Commercial products have utilized cationic polymers as structurants. For instance, U.S. Pat. No. 7,541,320 (Unilever) discloses a cationically modified cellulose in a cleansing system that includes alkyl ether sulfate (3 EO), cocoamidopropylbetaine and cocoamidopropylhydroxysultaine, and as a conditioning active a non-volatile silicone. U.S. Pat. No. 4,298,494 (Lever Brothers) reports use of a cationic derivative of polygalactomannan gum to stabilize a sodium alkyl sulfate and alkyl ether sulfate surfactant system.

Another group of commercially popular structurants are the acrylic polymers, particularly those known as Carbomers. For example, U.S. Pat. No. 5,543,074 (Chesebrough-Ponds) and U.S. Pat. No. 5,977,039 (Helene Curtis) regulate silicone deposition through use of crosslinked polymers of acrylic acid, commercially available under the trademark Carbopol®. U.S. Pat. No. 6,001,344 (Unilever) utilizes structurant combinations of xanthan gum and Carbopol® for stabilizing liquid cleansing compositions. U.S. Pat. No. 6,906,016 (Unilever) reports liquid cleansers structured with soluble and water swellable starches combined with linear Cs-Ci3 fatty acids. U.S. Patent Application Publication 2010/0009891 (Unilever) reports personal care liquid compositions formulated with a bacterially produced microfibrous cellulose as a suspending system.

An approach to the suspending of insoluble materials in an aqueous cleansing formulation is disclosed in U.S. Pat. No. 5,154,847 to LaPetina, et al. LaPentina, et al. disclose an antidandruff shampoo comprising an anionic surfactant in an amount of about 5% to about 20% by weight; a particulate antidandruff agent in an amount of about 0.2% to about 5% by weight; a water insoluble suspending agent, solid at room temperature, selected from the group consisting of a suspending alkanolamide, a wax ester, and mixtures thereof, in an amount of about 1% to about 3% by weight; a cross-linked, neutralized polyacrylic acid resin in an amount of about 0.3% to about 1% by weight; and a liquid carrier.

Another approach to the suspending of insoluble materials in an aqueous cleansing formulation is disclosed in U.S. Pat. No. 8,642,056 to Souzy, et al. Souzy, et al. disclose a method for thickening a formulation, comprising contacting a cosmetic formulation with a direct aqueous emulsion of a polymer, followed by regulation of the pH to a value between 5 and 7, thereby forming a thickened formulation, wherein the emulsion is free from surfactants and organic solvents other than water and the polymer consists, expressed as a % by weight of each of the monomers therein, of: a) 20% to 60% by weight of methacrylic acid and/or acrylic acid, where the % by weight of acrylic acid, if present, compared to the total weight of acrylic acid and methacrylic acid is at least 50%, b) 40% to 80% by weight of at least one monomer chosen from among ethyl acrylate, butyl acrylate, and methyl methacrylate, c) 0.5% to 25% by weight of a monomer comprising a hydrophobic group, d) 0.05% to 22% by weight of 2-acrylamido-2-methylpropane sulfonic acid, and e) 0 to 1% by weight of at least one cross-linked monomer, wherein the monomer comprising a hydrophobic group has the general formula:

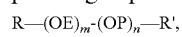

R—(OE)$_m$-(OP)$_n$—R', m and n are integers of less than or equal to 150, at least one of which is non-zero, OE and OP are respectively ethylene oxide and propylene oxide, R is a polymerizable group selected from the groups consisting of methacrylate and methacrylurethane groups, R' is a hydrophobic group having at least 6 and at most 36 carbon atoms.

Another approach to the suspending of insoluble materials in an aqueous cleansing formulation is disclosed in U.S. Pat. No. 6,106,816 to Hitchen. Hitchen discloses an aqueous conditioning shampoo composition comprising, in addition to water: (a) from 2 to 40% by weight of surfactant selected from the group consisting of anionic, nonionic and amphoteric surfactants, and mixtures thereof; (b) from 0.01 to 10% by weight of insoluble, non-volatile silicone which conditions hair; (c) from 0.01 to 3% by weight of titanium dioxide coated mica particles dispersed in the shampoo matrix; and (d) from 0.2 to 3% by weight of a crosslinked acrylic acid polymer for suspending the dispersed titanium dioxide coated mica particles and preventing them from settling in the composition as well as the insoluble, non-volatile silicone conditioning agent from creaming to the top of the composition on standing.

EP2933280 discloses aqueous shampoo compositions comprising HASE copolymers which comprise a) 10 to 80 percent by weight of methacrylic acid and, optionally, of acrylic acid; b) 15 to 80 percent by weight of at least one non-ionic vinyl monomer; c) 0.05 to 9.5 percent by weight of 2-acrylamido-2-methylpropane sulfonic acid or a salt thereof; d) 0.5 to 30 percent by weight of at least one monomer containing at least one hydrophobic group; and e) 0.01 to 5 percent by weight of at least one crosslinking monomer. The copolymers are said to be useful for thickening personal care or cosmetic formulations in acidic conditions.

Despite the prior art there remains a need for improved suspension and delivery of insoluble anti-dandruff actives from cleansing formulations, particularly improved delivery to the scalp.

We have now found that, for insoluble anti-dandruff ingredients, the use of the anti-settling, thickening polymer described herein significantly reduces the aggregation of suspended anti-dandruff ingredients both in-product and also on dilution of the shampoo, allowing individual particles of the anti-dandruff ingredient to be better deposited on the scalp. The reduced aggregation effectively increases the available surface area of the deposited anti-dandruff ingredient, thus improving its bioavailability by increasing the peak concentration of the anti-dandruff ingredient on the scalp following solubilisation within scalp secretions. This makes it more likely that the Minimum Inhibitory Concentration (MIC) can be reached. The MIC is defined as the absolute lowest concentration of active that provides complete microbial growth inhibition as indicated by the blue color of alamar blue under the tested condition.

Definition of the Invention

A first aspect of the invention provides an aqueous anti-dandruff shampoo composition which comprises:
(I) a cleansing surfactant selected from the group consisting of anionic surfactant, zwitterionic or amphoteric surfactant and nonionic surfactant;
(II) suspended particles of an anti-dandruff agent,
(III) an anti-settling, thickening polymer,
wherein the anti-settling, thickening polymer, comprises:
(a) 40 to 74.5 wt % of structural units of $C_{1-4}$ alkyl acrylate;
(b) 20 to 50 wt % of structural units of methacrylic acid;
(c) 0.2 to <5 wt % of structural units of 2-acrylamido-2-methylpropane sulfonic acid (AMPS);
(d) 5 to 25 wt % of structural units of a specialized associated monomer having the following structure:

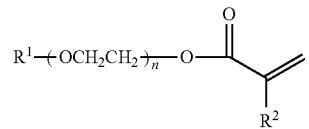

wherein $R^1$ is a linear saturated $C_{10-24}$ alkyl group; wherein $R^2$ is a hydrogen or a methyl group (preferably, wherein $R^2$ is a methyl group); and wherein n is an average of 20 to 28; with the proviso that the structural units of the specialized associated monomer (d) are derived from one of (i) a single specialized associated monomer (preferably, a single specialized associated monomer wherein $R^1$ is selected from the group consisting of a linear saturated $C_{12}$ alkyl group, a linear saturated $C_{18}$ alkyl group and a linear saturated $C_{22}$ alkyl group; more preferably, a single specialized associated monomer wherein $R^1$ is selected from the group consisting of a linear saturated $C_{12}$ alkyl group and a linear saturated $C_{18}$ alkyl group); (ii) two specialized associated monomers, wherein $R^1$ is, respectively, a linear saturated $C_{12}$ and a linear saturated $C_{18}$ alkyl group; or (iii) two specialized associated monomers, wherein $R^1$ is, respectively, a linear saturated $C_{18}$ alkyl group and a linear saturated $C_{22}$ alkyl group;
(e) 0 to 1 wt % of structural units of acrylic acid; and
(f) 0 to 2 wt % of structural units of multi-ethylenically unsaturated crosslinking monomer or chain transfer agent; and
wherein the sum of the weight percentages of structural units (a)-(f) is equal to 100 wt % of the anti-settling, thickening polymer.

A second aspect of the invention provides a composition as defined by the first aspect of the invention, for use in a method of treating a surface, selected from hair and scalp, wherein the method comprises the step of applying to the surface the composition of the first aspect.

A third aspect of the invention provides a use of these compositions for the treatment of inflammatory skin conditions such as scalp itch and dandruff.

The method preferably further comprises the additional step of rinsing the surface with water. The method is preferably a method of providing anti-fungal efficacy to the surface.

GENERAL DESCRIPTION OF THE INVENTION

The aqueous composition of the present invention contains an anti-settling thickening polymer, for use in the treatment of surfaces.

The aqueous composition is preferably a cleansing composition. More preferably, the aqueous composition is selected from a personal care cleansing composition and a home care cleansing composition, and is most preferably a personal care cleaning composition. Most preferably the composition is a hair cleansing composition, preferably a shampoo A preferred composition is a rinse off composition.

The Anti-Settling Thickening Polymer

The anti-settling, thickening polymer for use in the aqueous compositions of the invention, comprises: (a) 40 to 74.5 wt % (preferably, 45 to 69.5 wt %; more preferably, 50 to 65 wt %; most preferably, 52 to 60 wt %) of structural units of $C_{1-4}$ alkyl acrylate (preferably, $C_{2-4}$ alkyl acrylate; more preferably, $C_{2-3}$ alkyl acrylate; most preferably, ethyl acrylate); (b) 20 to 50 wt % (preferably, 25 to 45 wt %; more preferably, 25 to 40 wt %; most preferably, 30 to 35 wt %) of structural units of methacrylic acid; (c) 0.2 to <5 wt % (preferably, 0.5 to 3 wt %; more preferably, 0.75 to 2.0 wt %; most preferably, 0.75 to 1.5 wt %) of structural units of 2-acrylamido-2-methylpropane sulfonic acid (AMPS); (d) 5 to 25 wt % (preferably, 7.5 to 22.5 wt %; more preferably, 10 to 20 wt %; most preferably, 12.5 to 18 wt %) of structural units of a specialized associated monomer having the following structure (formula 1):—

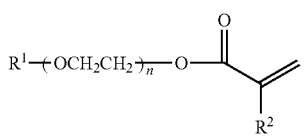

wherein $R^1$ is a linear saturated $C_{10-24}$ alkyl group; wherein $R^2$ is a hydrogen or a methyl group (preferably, wherein $R^2$ is a methyl group); and wherein n is an average of 20 to 28; with the proviso that the structural units of the specialized associated monomer (d) are derived from one of (i) a single specialized associated monomer (preferably, a single specialized associated monomer wherein $R^1$ is selected from the group consisting of a linear saturated $C_{12}$ alkyl group, a linear saturated $C_{18}$ alkyl group and a linear saturated $C_{22}$ alkyl group; more preferably, a single specialized associated monomer wherein $R^1$ is selected from the group consisting of a linear saturated $C_{12}$ alkyl group and a linear saturated $C_{18}$ alkyl group); (ii) two specialized associated monomers, wherein $R^1$ is, respectively, a linear saturated $C_{12}$ and a linear saturated $C_{18}$ alkyl group; or (iii) two specialized associated monomers, wherein $R^1$ is, respectively, a linear saturated $C_{18}$ alkyl group and a linear saturated $C_{22}$ alkyl group; (e) 0 to 1 wt % (preferably, 0 to 0.1 wt %; more preferably, 0 to 0.01 wt %; most preferably, 0) of structural units of acrylic acid; and (f) 0 to 2 wt % (preferably, 0 to 0.1 wt %; more preferably, 0 to 0.001 wt %; most preferably, 0 wt %) of structural units of multi-ethylenically unsaturated crosslinking monomer and chain transfer agent; wherein the sum of the weight percentages of structural units (a)-(f) is equal to 100 wt % of the anti-settling, thickening polymer.

Preferably, the anti-settling, thickening polymer for use in the aqueous compositions of the invention, comprises: (a) 50 to 65 wt % of structural units of ethyl acrylate; (b) 25 to 40 wt % of structural units of methacrylic acid; (c) 0.75 to 2.0 wt % of structural units of 2-acrylamido-2-methylpropane sulfonic acid (AMPS); (d) 10 to 20 wt % of structural units of the specialized associated monomer; (e) 0 to 0.1 wt % of structural units of acrylic acid; and (f) 0 to 0.1 wt % (preferably, 0 to 0.001 wt %; more preferably, 0 wt %) of structural units of multi-ethylenically unsaturated crosslinking monomer and chain transfer agent; wherein the sum of the weight percentages of structural units (a)-(f) is equal to 100 wt % anti-settling, thickening polymer.

Preferably, the anti-settling thickening polymer for use in the aqueous compositions of the invention has a weight average molecular weight of 5,000,000 to 400,000,000 Daltons. More preferably, the anti-settling, thickening polymer for use in the aqueous compositions of the invention has a weight average molecular weight of 25,000,000 to 300,000,000 Daltons. Most preferably, the anti-settling, thickening polymer for use in the aqueous compositions of the invention has a weight average molecular weight of 175,000,000 to 275,000,000 Daltons.

In reference to the anti-settling thickening polymer the weight average molecular weight refers to the weight average molecular weight as measured using asymmetric flow field flow fractionation (AF4) with inline Multi-Angle Light Scattering (MALS) and differential Refractive Index (RI) detections. The AF4 instrument used consisted of an Eclipse™ DualTec™ separation system (from Wyatt Technology Corp.) that was coupled in series to an 18 angle multi-angle light scattering (MALS) detector (DAWN HELOS II; from Wyatt Technology Corp.) and a differential refractometer (RI) (Optilab rEX; from Wyatt Technology Corp.). Flows through the AF4 instrument were provided using an Agilent Technologies 1200 series isocratic pump equipped with a micro-vacuum degasser. All injections were performed with an auto sampler (Agilent Technologies 1200 series). Data from the AF4 instrument were collected and processed using Astra software version 7.0.1.23 (from Wyatt Technology Corp.). Samples were prepared at a concentration of 1 mg/mL in 20 mM ammonium acetate solution at pH 10 (filtered with a 1.2 μm pore nylon membrane). Samples (25 μL) were injected into the standard separation channel system (25 cm long and a width dimension starting at 2.15 cm and reducing to 0.3 cm over the length) with a channel thickness of 350 μm and equipped with a 10 kDA cutoff regenerated cellulose ultrafiltration membrane (Wyatt Technology). The mobile phase used for the AF4 analysis was 20 mM ammonium acetate solution at pH 10. Separation was performed with an applied channel flow of 1 mL/min. The sample was introduced to the channel with a focus flow at 1.7 mL/min for 3 minutes. The elution flow as then started at 0.5 mL/min for 3 minutes and then followed by a linearly decreasing cross flow gradient (from 0.5 mL/min to 0.05 mL/min over 12 minutes), then a hold at 0.05 mL/min for another 5 minutes. The average molecular weight was calculated using Astra software version 7.0.1.23 after subtracting a blank injection with a refractive index increment (dn/dc) of 0.190 mL/g for all calculation with Berry model $2^{nd}$ order fit. Molecular weights are reported herein in units of Daltons.

Preferably, the structural units of $C_{1-4}$ alkyl acrylate in the anti-settling, thickening polymer for use in the aqueous compositions of the invention are structural units of $C_{2-4}$ alkyl acrylate. More preferably, the structural units of $C_{1-4}$ alkyl acrylate in the anti-settling, thickening polymer for use in the aqueous compositions of the invention are structural units of $C_{2-3}$ alkyl acrylate. Most preferably, the structural units of $C_{1-4}$ alkyl acrylate in the anti-settling, thickening polymer for use in the aqueous compositions of the invention are structural units of ethyl acrylate.

Preferably, the anti-settling, thickening polymer for use in the aqueous compositions of the invention comprises 40 to 74.5 wt % of structural units of $C_{1-4}$ alkyl acrylate (preferably, $C_{2-4}$ alkyl acrylate; more preferably, $C_{2-3}$ alkyl acrylate; most preferably, ethyl acrylate). More preferably, the anti-settling, thickening polymer for use in the aqueous compositions of the invention comprises 45 to 69.5 wt % of structural units of $C_{1-4}$ alkyl acrylate (preferably, $C_{2-4}$ alkyl acrylate; more preferably, $C_{2-3}$ alkyl acrylate; most preferably, ethyl acrylate). Still more preferably, the anti-settling, thickening polymer for use in the aqueous compositions of the invention comprises 50 to 65 wt % of structural units of $C_{1-4}$ alkyl acrylate (preferably, $C_{2-4}$ alkyl acrylate; more preferably, $C_{2-3}$ alkyl acrylate; most preferably, ethyl acrylate). Most preferably, the anti-settling, thickening polymer for use in the aqueous compositions of the invention comprises 52 to 60 wt % of structural units of $C_{1-4}$ alkyl acrylate (preferably, $C_{2-4}$ alkyl acrylate; more preferably, $C_{2-3}$ alkyl acrylate; most preferably, ethyl acrylate).

Preferably, the anti-settling, thickening polymer for use in the aqueous compositions of the invention comprises 20 to 50 wt % of structural units of methacrylic acid. More preferably, the anti-settling, thickening polymer for use in the aqueous compositions of the invention comprises 25 to 45 wt % of structural units of methacrylic acid. Still more preferably, the anti-settling, thickening polymer for use in the aqueous compositions of the invention comprises 25 to 40 wt % of structural units of methacrylic acid. Most preferably, the anti-settling, thickening polymer for use in the aqueous compositions of the invention comprises 30 to 35 wt % of structural units of methacrylic acid.

Preferably, the anti-settling, thickening polymer for use in the aqueous compositions of the invention comprises 0.2 to <5 wt % of structural units of 2-acrylamido-2-methylpropane sulfonic acid (AMPS). More preferably, the anti-settling, thickening polymer for use in the aqueous compositions of the invention comprises 0.5 to 3 wt % of structural units of 2-acrylamido-2-methylpropane sulfonic acid (AMPS). Even more preferably, the anti-settling, thickening polymer for use in the aqueous compositions of the invention comprises 0.5 to 1.5 wt % of structural units of 2-acrylamido-2-methylpropane sulfonic acid (AMPS). Most preferably, the anti-settling, thickening polymer for use in the aqueous compositions of the invention comprises 0.5 to 1.0, of structural units of 2-acrylamido-2-methylpropane sulfonic acid (AMPS).

Preferably, the anti-settling, thickening polymer for use in the aqueous compositions of the invention comprises 5 to 25 wt % of structural units of a specialized associated monomer having the following structure:

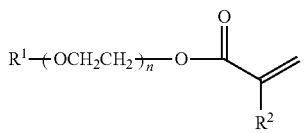

wherein $R^1$ is a linear saturated $C_{10-24}$ alkyl group; wherein $R^2$ is a hydrogen or a methyl group (preferably, wherein $R^2$ is a methyl group); and wherein n is an average of 20 to 28; with the proviso that the structural units of the specialized associated monomer (d) are derived from one of (i) a single specialized associated monomer (preferably, a single specialized associated monomer wherein $R^1$ is selected from the group consisting of a linear saturated $C_{12}$ alkyl group, a linear saturated $C_{18}$ alkyl group and a linear saturated $C_{22}$ alkyl group; more preferably, a single specialized associated monomer wherein $R^1$ is selected from the group consisting of a linear saturated $C_{12}$ alkyl group and a linear saturated $C_{18}$ alkyl group); (ii) two specialized associated monomers, wherein $R^1$ is, respectively, a linear saturated $C_{12}$ and a linear saturated $C_{18}$ alkyl group; or (iii) two specialized associated monomers, wherein $R^1$ is, respectively, a linear saturated $C_{18}$ alkyl group and a linear saturated $C_{22}$ alkyl group. More preferably, the anti-settling, thickening polymer for use in the aqueous compositions of the invention comprises 7.5 to 22.5 wt % of structural units of a specialized associated monomer having the following structure:

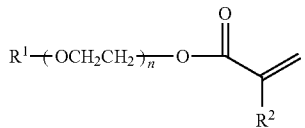

wherein $R^1$ is a linear saturated $C_{10-24}$ alkyl group; wherein $R^2$ is a hydrogen or a methyl group (preferably, wherein $R^2$ is a methyl group); and wherein n is an average of 20 to 28; with the proviso that the structural units of the specialized associated monomer (d) are derived from one of (i) a single specialized associated monomer (preferably, a single specialized associated monomer wherein $R^1$ is selected from the group consisting of a linear saturated $C_{12}$ alkyl group, a linear saturated $C_{18}$ alkyl group and a linear saturated $C_{22}$ alkyl group; more preferably, a single specialized associated monomer wherein $R^1$ is selected from the group consisting of a linear saturated $C_{12}$ alkyl group and a linear saturated $C_{18}$ alkyl group); (ii) two specialized associated monomers, wherein $R^1$ is, respectively, a linear saturated $C_{12}$ and a linear saturated $C_{18}$ alkyl group; or (iii) two specialized associated monomers, wherein $R^1$ is, respectively, a linear saturated $C_{18}$ alkyl group and a linear saturated $C_{22}$ alkyl group. Still more preferably, the anti-settling, thickening polymer for use in the aqueous compositions of the invention comprises 10 to 20 wt % of structural units of a specialized associated monomer having the following structure:

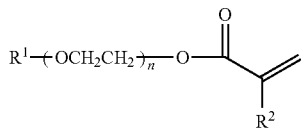

wherein $R^1$ is a linear saturated $C_{10-24}$ alkyl group; wherein $R^2$ is a hydrogen or a methyl group (preferably, wherein $R^2$ is a methyl group); and wherein n is an average of 20 to 28; with the proviso that the structural units of the specialized associated monomer (d) are derived from one of (i) a single specialized associated monomer (preferably, a single specialized associated monomer wherein $R^1$ is selected from the group consisting of a linear saturated $C_{12}$ alkyl group, a linear saturated $C_{18}$ alkyl group and a linear saturated $C_{22}$ alkyl group; more preferably, a single specialized associated monomer wherein $R^1$ is selected from the group consisting of a linear saturated $C_{12}$ alkyl group and a linear saturated $C_{18}$ alkyl group); (ii) two specialized associated monomers, wherein $R^1$ is, respectively, a linear saturated $C_{12}$ and a linear saturated $C_{18}$ alkyl group; or (iii) two specialized associated monomers, wherein $R^1$ is, respectively, a linear saturated $C_{18}$ alkyl group and a linear saturated $C_{22}$ alkyl group. Most preferably, the anti-settling, thickening polymer for use in the aqueous compositions of the invention comprises 12.5 to 18 wt % of structural units of a specialized associated monomer having the following structure:

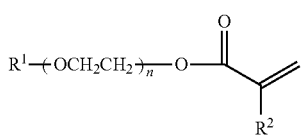

wherein $R^1$ is a linear saturated $C_{10-24}$ alkyl group; wherein $R^2$ is a hydrogen or a methyl group (preferably, wherein $R^2$ is a methyl group); and wherein n is an average of 20 to 28; with the proviso that the structural units of the specialized associated monomer (d) are derived from one of (i) a single specialized associated monomer (preferably, a single specialized associated monomer wherein $R^1$ is selected from the group consisting of a linear saturated $C_{12}$ alkyl group, a linear saturated $C_{18}$ alkyl group and a linear saturated $C_{22}$ alkyl group; more preferably, a single specialized associated monomer wherein $R^1$ is selected from the group consisting of a linear saturated $C_{12}$ alkyl group and a linear saturated $C_{18}$ alkyl group); (ii) two specialized associated monomers, wherein $R^1$ is, respectively, a linear saturated $C_{12}$ and a linear saturated $C_{18}$ alkyl group; or (iii) two specialized associated monomers, wherein $R^1$ is, respectively, a linear saturated $C_{18}$ alkyl group and a linear saturated $C_{22}$ alkyl group.

Preferably, the anti-settling, thickening polymer for use in the aqueous compositions of the invention includes 0 to 1 wt % of structural units of acrylic acid. More preferably, the anti-settling, thickening polymer for use in the aqueous compositions of the invention includes 0 to 0.1 wt % of structural units of acrylic acid. Still more preferably, anti-settling, thickening polymer for use in the aqueous compositions of the invention contains 0 to 0.01 wt % of structural units of acrylic acid. Yet still more preferably, the anti-settling, thickening polymer for use in the aqueous compositions of the invention includes less than the detectable limit of structural units of acrylic acid. Most preferably, the anti-settling, thickening polymer for use in the aqueous compositions of the invention contains 0 wt % structural units of acrylic acid.

Preferably, the anti-settling, thickening polymer for use in the aqueous compositions of the invention comprises 0 to 2 wt % of structural units of multi-ethylenically unsaturated crosslinking monomer and chain transfer agent. More preferably, the anti-settling, thickening polymer for use in the aqueous compositions of the invention comprises 0 to 0.1 wt % of structural units of multi-ethylenically unsaturated crosslinking monomer and chain transfer agent. Still more preferably, the anti-settling, thickening polymer for use in the aqueous compositions of the invention comprises 0 to 0.001 wt % of structural units of multi-ethylenically unsaturated crosslinking monomer and chain transfer agent. Yet still more preferably, the anti-settling, thickening polymer for use in the aqueous compositions of the invention includes less than the detectable limit of structural units of multi-ethylenically unsaturated crosslinking monomer and chain transfer agent. Most preferably, the anti-settling, thickening polymer for use in the aqueous compositions of the invention contains 0 wt % structural units of multi-ethylenically unsaturated crosslinking monomer and chain transfer agent.

Preferably, the anti-settling, thickening polymer for use in the aqueous compositions of the invention includes less than 0.001 wt % of structural units of multi-ethylenically unsaturated crosslinking monomer. More preferably, the anti-settling, thickening polymer for use in the aqueous compositions of the invention includes less than 0.0001 wt % of structural units of multi-ethylenically unsaturated crosslinking monomer. Still more preferably, anti-settling, thickening polymer for use in the aqueous compositions of the invention contains less than the detectable limit of structural units of multi-ethylenically unsaturated crosslinking monomer. Most preferably, the anti-settling, thickening polymer for use in the aqueous compositions of the invention includes 0 wt % of structural units of multi-ethylenically unsaturated crosslinking monomer.

Preferably, the anti-settling, thickening polymer for use in the aqueous compositions of the invention includes less than 0.1 wt % of structural units of chain transfer agent. More preferably, the anti-settling, thickening polymer for use in the aqueous compositions of the invention includes less than 0.001 wt % of structural units of chain transfer agent. Still more preferably, anti-settling, thickening polymer for use in the aqueous compositions of the invention contains less than the detectable limit of structural units of chain transfer agent. Most preferably, the anti-settling, thickening polymer for use in the aqueous compositions of the invention includes 0 wt % of structural units of chain transfer agent.

Preferably, the anti-settling, thickening polymer for use in the aqueous compositions of the invention includes less than 0.001 wt % of structural units of multi-ethylenically unsaturated crosslinking monomer and less than 0.1 wt % of structural units of chain transfer agent. More preferably, the anti-settling, thickening polymer for use in the aqueous compositions of the invention includes less than 0.0001 wt % of structural units of multi-ethylenically unsaturated crosslinking monomer and less than 0.01 wt % of structural units of chain transfer agent. Still more preferably, anti-settling, thickening polymer for use in the aqueous compositions of the invention contains less than the detectable limit of structural units of multi-ethylenically unsaturated crosslinking monomer and less than the detectable limit of structural units of chain transfer agent. Most preferably, the anti-settling, thickening polymer for use in the aqueous compositions of the invention includes 0 wt % of structural units of multi-ethylenically unsaturated crosslinking monomer and includes 0 wt % of structural units of chain transfer agents.

One of ordinary skill in the art will know to select appropriate multi-ethylenically unsaturated crosslinking monomers to provide any structural units of multi-ethylenically unsaturated crosslinking monomer in the anti-settling, thickening polymer for use in the aqueous compositions of the invention. Structural units of multi-ethylenically unsaturated crosslinking monomer may include for example those derived from polyunsaturated monomer components including, polyunsaturated aromatic monomers (e.g., divinyl benzene, divinyl naphthalene, trivinyl benzene); polyunsaturated alicyclic monomers (e.g., 1,2,4-trivinylcyclohexane); difunctional esters of phthalic acid (e.g., diallyl phthalate); polyunsaturated aliphatic monomers (e.g., isoprene, butadiene, 1,5-hexadiene, 1,5,9-decatriene, 1,9-decadiene, 1,5-heptadiene); polyalkenyl ethers (e.g., triallyl pentaerythritol, diallyl pentaerythritol, diallyl sucrose, octaally sucrose, trimethylolpropane diallyl ether); polyunsaturated esters of polyalcohols or polyacids (e.g., 1,6-hexanediol di(meth)acrylate, tetramethylene tri(meth)acrylate, allyl acrylate, diallyl itaconate, diallyl fumarate, diallyl maleate, trimethylolpropane tri(meth)acrylate, trimethylolpropane di(meth)acrylate, polyethylene glycol di(meth)acrylate); alkylene bisacrylamides (e.g., methylene bisacrylamide, propylene bisacrylamide); hydroxy and carboxy derivatives of methylene bisacrylamide (e.g., N,N'-bismethylol methylene bisacrylamide); polyethyleneglycol di(meth)acrylates (e.g., ethyleneglycol di(meth)acrylate, diethyleneglycol di(meth)acrylate, triethyleneglycol di(meth)acrylate); polyunsaturated silanes (e.g., dimethyldivinylsilane, methyltrivinylsilane, allyldimethylvinylsilane, diallydimethylsilane, tetravinylsilane); polyunsaturated stannanes (e.g., tetraallyl tin, diallyldimethyl tin) and the like.

One of ordinary skill in the art will know to select appropriate chain transfer agents to provide any structural units of chain transfer agents in the anti-settling, thickening polymer for use in the aqueous compositions of the invention. Structural units of chain transfer agents may monomer include those derived from a variety of thio and disulfide containing compounds (e.g., $C_{1-18}$ alkyl mercaptans, mercaptocarboxylic acids, mercaptocarboxylic esters, thioesters, $C_{1-18}$ alkyl disulfides, aryldisulfides, polyfunctional thiols); phosphites and hypophosphites; haloalkyl compounds (e.g., carbon tetrachloride, bromotrichloromethane) and unsaturated chain transfer agents (e.g., alpha-methylstyrene).

Preferably, the shampoo of the present invention, includes from 0.05 to 4 wt % of the anti-settling, thickening polymer more preferably from 0.05 to 3 wt %, still more preferably from 0.1 to 1 wt % and most preferably from 0.2 to 0.8 wt % by weight of total composition.

The Antidandruff Agent

The composition of the invention comprises suspended particles of an antidandruff agent.

Antidandruff agents are compounds that are active against dandruff and are typically antimicrobial agents, preferably antifungal agents. Antidandruff agents typically display a minimum inhibitory concentration of about 50 mg/ml or less against *Malassezia*.

The total amount of anti-dandruff agent is preferably present at levels of from 0.01% to 30% by weight, more preferably 0.05% to 10%, even more preferably 0.1% to 5% and most preferably 0.2% to 4% by weight of the total composition.

However, where the anti-dandruff agent is zinc pyrithione, preferred levels in compositions of the invention are from 0.1 to 3%, more preferably from 0.2 to 2%, most preferably from 0.5 to 1.5%, by weight based on the total weight of the composition.

The antidandruff agent is selected such that it is insoluble in the composition of the invention and, therefore, capable of forming suspended particles. The solubility of the anti-dandruff agent will vary according to the presence and level of the other ingredients. The antidandruff agent should be insoluble at temperature of normal use and storage, preferably from 15 to 25 degrees C.

The antidandruff agent is preferably selected from metal pyrithiones, azoles, octopirox (piroctone olamine), selenium sulfide, salicylic acid and combinations thereof, preferably metal pyrithiones, azoles and octopirox. The most preferred antidandruff agent is selected from metal pyrithiones, most preferably is zinc pyrithione.

Suitable metal pyrithiones include zinc pyrithione, copper pyrithione, silver pyrithione, zirconium pyrithione, and mixtures thereof. The most preferred metal pyrithione is zinc pyrithione.

The particles of zinc pyrithione may be amorphous, or may take various regular or irregular crystalline forms such as rods, needles, blocks, platelets and mixtures thereof. The average particle diameter of the zinc pyrithione particles (maximum dimension) is typically from about 0.1 to about 50 μm, preferably from about 0.1 m to about 10 μm, more preferably from about 0.1 μm to about 5 μm as determined, for example, using a Horiba LA-910 Laser scattering particle size distribution analyzer.

Azole based antifungal agents include ketoconazole and climbazole, preferably climbazole.

Other suitable antidandruff agents are octopirox (piroctone olamine), selenium sulfide and salicylic acid.

Additional Anti-Dandruff Agents

The compositions of the invention may further include a further anti-dandruff agent that is soluble within the cleansing compositions of the present invention. These are preferably selected from azoles (preferably selected from ketoconazole and climbazole), octopirox (piroctone olamine), salicylic acid and combinations thereof, where soluble in the inventive composition.

Optional Zinc Salts

The compositions of the invention advantageously include a zinc salt. The additional zinc salt may suitably be selected from zinc salts of organic acids, zinc salts of inorganic acids, zinc oxides, zinc hydroxides and mixtures thereof.

Examples of additional zinc salts for use in the invention include zinc oxide, zinc pyrrolidone carboxylic acid, zinc citrate, zinc carbonate, zinc chloride, zinc sulphate, zinc glycinate, zinc acetate, zinc lactate, and mixtures thereof.

Additional zinc salts for use in the formulated products of the invention preferably have a zinc mass % of at least 25%, more preferably at least 30% (based on total mass of the zinc salt).

Additional zinc salts for use in the invention preferably have a solubility in water of 20 g/l or less, more preferably 0.1 g/l or less at 25° C.

Examples of preferred additional zinc salts for use in the invention include zinc oxide, zinc pyrrolidone carboxylic acid, zinc citrate, zinc carbonate and mixtures thereof.

The level of additional zinc salt(s) in compositions of the invention generally ranges from 0.1 to 5%, and preferably ranges from 0.2 to 3%, more preferably from 0.25 to 2.5%, by weight based on the total weight of the composition.

In a particularly preferred composition according to the invention the additional zinc salt is selected from zinc oxide, zinc pyrrolidone carboxylic acid, zinc citrate, zinc carbonate and mixtures thereof; at a level ranging from about 0.25 to about 2.5% by weight based on the total weight of the composition.

The Cleansing Surfactant

The composition of the present invention comprises a surfactant selected from the group consisting of anionic surfactants, nonionic surfactants, zwitterionic surfactants and mixtures thereof.

Preferably, the cleansing surfactant is selected from the group consisting of sodium lauryl sulphate, sodium lauryl ether sulphate, sodium lauryl ether sulphosuccinate, ammonium lauryl sulphate, ammonium lauryl ether sulphate, sodium cocoyl isethionate and lauryl ether carboxylic acid, coco betaine, cocamidopropyl betaine, sodium cocoamphoacetate and mixtures thereof.

Preferably, mixtures of any of the anionic, non-ionic and amphoteric cleansing surfactants has a ratio of primary to secondary surfactant of between 1:1-10:1, more preferably 2:1-9:1 and most preferably 3:1-8:1, based on the inclusion weight of the cleansing surfactant in the shampoo composition.

Preferably, the composition of the present invention comprises from 1 to 50%, preferably from 2 to 40%, more preferably from 4 to 25% of total surfactant, based on the total weight of the composition.

Cosmetic Ingredient—General

The composition of the present invention preferably comprises a cosmetic ingredient. Preferably the cosmetic ingredient selected from the group consisting of a silicone, an antibacterial agent, a foam booster, a perfume, encapsulates (for example encapsulated fragrance) a dye, a colouring agent, a pigment, a preservative, a thickener, a protein, a phosphate ester, a buffering agent, a pH adjusting agent, a pearlescer (for example; mica, titanium dioxide, titanium dioxide coated mica, ethylene glycol distearate (INCI glycol distearate)) and/or opacifier, a viscosity modifier, an emollient, a sunscreen, an emulsifier, a sensate active (for example menthol and menthol derivatives), vitamins, mineral oils, essential oils, lipids, natural actives, glycerine, natural hair nutrients such as botanicals, fruit extracts, sugar derivatives and amino acids, microcrystalline cellulose and mixtures thereof.

Preferably, the aqueous composition of the present invention includes from 0.01 to 20 wt % of the at least one cosmetic ingredient, more preferably from 0.05 to 10 wt %, still more preferably from 0.075 to 7.5 wt % and most preferably, from 0.1 to 5 wt % of the at least one cosmetic ingredient, by weight of the total composition.

Synergistic Anti-Microbial Compounds

The composition of the present invention may also comprise synergistic antimicrobial compounds that give synergistic antimicrobial benefit when used in combination with the anti-dandruff active (for example zinc pyrithione) to enhance its properties and further inhibit the growth of *Malassezia furfur*. Non-limiting examples of these compounds include compounds of the benzophenone class (e.g. benzophenone-1 and benzophenone-2), a class of compounds having alcoholic groups (e.g. honokiol, magnolol or paeonol), Piperazines and a phenolic compound found in natural plant extract viz. thymol.

Other Ingredients

The composition may additionally comprise a vitamin B3 compound. The preferred vitamin B3 compound is niacinamide.

Niacinamide has the structure as given below:

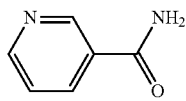

Niacinamide is known for secretion of AMPs (Anti-Microbial Proteins) from keratinocytes. The AMPs thus secreted provides for improving the immunity of the external surface of the body e.g. on the scalp. Thus with the use of niacinamide in the composition of the invention the anti-dandruff efficacy is expected to be enhanced not just through anti-fungal activity of the composition of the invention but by providing a boost to the scalp's own protection shield against germs, through use of niacinamide. It is expected that this combination could provide further long-lasting protection e.g. up to 24 hours of protection against germs.

Niacinamide is preferably present in 0.1 to 5%, more preferably 0.5 to 5%, further more preferably 0.5 to 3%, and optimally 1.0 to 3.0% by weight of the composition.

Silicone

A preferred cosmetic ingredient is silicone.

The compositions of the invention can contain, emulsified droplets of a silicone conditioning agent, for enhancing conditioning performance.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188.

The viscosity of the emulsified silicone itself (not the emulsion or the final hair conditioning composition) is typically at least 10,000 cst at 25° C. the viscosity of the silicone itself is preferably at least 60,000 cst, most preferably at least 500,000 cst, ideally at least 1,000,000 cst. Preferably the viscosity does not exceed $10^9$ cst for ease of formulation.

Emulsified silicones for use in the shampoo compositions of the invention will typically have a D90 silicone droplet size in the composition of less than 30, preferably less than 20, more preferably less than 10 micron, ideally from 0.01 to 1 micron. Silicone emulsions having an average silicone droplet size (D50) of 0.15 micron are generally termed microemulsions.

Silicone particle size may be measured by means of a laser light scattering technique, for example using a 2600D Particle Sizer from Malvern Instruments.

Examples of suitable pre-formed emulsions include Xiameter MEM 1785 and microemulsion DC2-1865 available from Dow Corning. These are emulsions/microemulsions of dimethiconol. Cross-linked silicone gums are also available in a pre-emulsified form, which is advantageous for ease of formulation.

A further preferred class of silicones for inclusion in shampoos and conditioners of the invention are amino functional silicones. By "amino functional silicone" is meant a silicone containing at least one primary, secondary or tertiary amine group, or a quaternary ammonium group. Examples of suitable amino functional silicones include: polysiloxanes having the CTFA designation "amodimethicone".

Specific examples of amino functional silicones suitable for use in the invention are the aminosilicone oils DC2-8220, DC2-8166 and DC2-8566 (all ex Dow Corning).

Suitable quaternary silicone polymers are described in EP-A-0 530 974. A preferred quaternary silicone polymer is K3474, ex Goldschmidt.

Also suitable are emulsions of amino functional silicone oils with non ionic and/or cationic surfactant.

Pre-formed emulsions of amino functional silicone are also available from suppliers of silicone oils such as Dow Corning and General Electric. Specific examples include DC939 Cationic Emulsion and the non-ionic emulsions DC2-7224, DC2-8467, DC2-8177 and DC2-8154 (all ex Dow Corning).

The total amount of silicone is preferably from 0.01 wt % to 10% wt of the total composition more preferably from 0.1 wt % to 5 wt %, most preferably 0.5 wt % to 3 wt % is a suitable level.

In a preferred embodiment, the aqueous composition of the invention comprises at least one insoluble conditioning agent and at least one other cosmetic ingredient. Preferably, the at least one oily conditioning agent is selected from a silicone and a non-silicone oily conditioning agent.

pH of Compositions

The composition of the present invention preferably has a pH of from 3 to 7, preferably 4 to 7, more preferably 4 to 6.5, most preferably from 4.2 to 6.5.

Shampoos

Shampoo compositions of the invention are generally aqueous, i.e. they have water or an aqueous solution or a lyotropic liquid crystalline phase as their major component.

Suitably, the shampoo composition will comprise from 50 to 98%, preferably from 60 to 92% water by weight based on the total weight of the composition.

Surfactants are compounds which have hydrophilic and hydrophobic portions that act to reduce the surface tension of the aqueous solutions they are dissolved in. Shampoo compositions according to the invention will generally comprise one or more cleansing surfactants, which are cosmetically acceptable and suitable for topical application to the hair. The cleansing surfactant may be chosen from anionic, non-ionic, amphoteric and zwitterionic compounds and mixtures thereof.

The total amount of cleansing surfactant in a shampoo composition for use in the invention is generally from 1 to 50%, preferably from 2 to 40%, more preferably from 4 to 25% by total weight surfactant based on the total weight of the composition.

Non-limiting examples cleansing surfactants include anionic cleansing surfactants include; alkyl sulphates, alkyl ether sulphates, alkaryl sulphonates, N-alkyl sarcosinates, alkyl phosphates, alkyl ether phosphates, acyl amino acid based surfactants, alkyl ether carboxylic acids, acyl taurates, acyl glutamates, alkyl glycinates and salts thereof, especially their sodium, magnesium, ammonium and mono-, di- and triethanolamine salts. The alkyl and acyl groups in the preceding list generally contain from 8 to 18, preferably from 10 to 16 carbon atoms and may be unsaturated. The alkyl ether sulphates, alkyl ether phosphates and alkyl ether carboxylic acids and salts thereof may contain from 1 to 20 ethylene oxide or propylene oxide units per molecule.

Further non-limiting examples of cleansing surfactants may include non-ionic cleansing surfactants including; aliphatic ($C_8$-$C_{18}$) primary or secondary linear or branched chain alcohols with alkylene oxides, usually ethylene oxide and generally having from 6 to 30 ethylene oxide groups. Other representative cleansing surfactants include mono- or di-alkyl alkanolamides (examples include coco mono-ethanolamide and coco mono-isopropanolamide) and alkyl polyglycosides (APGs). Suitable alkyl polyglycosides for use in the invention are commercially available and include for example those materials identified as: Plantapon 1200 and Plantapon 2000 ex BASF. Other sugar-derived surfactants, which can be included in compositions for use in the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl) glucamide.

Additional non-limiting examples of cleansing surfactants may include amphoteric or zwitterionic cleansing surfactants including; alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms.

Typical cleansing surfactants for use in shampoo compositions for use in the invention include sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium cocoyl isethionate, sodium lauryl isethionate, lauryl ether carboxylic acid and sodium N-lauryl sarcosinate, sodium pareth sulphate, cocodimethyl sulphopropyl betaine, lauryl betaine, coco betaine, cocamidopropyl betaine, sodium cocoamphoacetate.

Preferred cleansing surfactants are sodium lauryl sulphate, sodium lauryl ether sulphate, sodium lauryl ether sulphosuccinate, ammonium lauryl sulphate, ammonium lauryl ether sulphate, sodium cocoyl isethionate and lauryl ether carboxylic acid, coco betaine, cocamidopropyl betaine, sodium cocoamphoacetate.

Mixtures of any of the foregoing anionic, non-ionic and amphoteric cleansing surfactants may also be suitable, preferably where the primary to secondary surfactant ratio is between 1:1-10:1, more preferably 2:1-9:1 and most preferably 3:1-8:1, based on the inclusion weight of the cleansing surfactant in the shampoo composition.

Optionally, a shampoo composition for use in the invention may contain further ingredients, (non-limiting examples of which are described below) to enhance performance and/or consumer acceptability.

Cationic polymers are preferred ingredients in a shampoo composition for use in the invention for enhancing conditioning performance.

Suitable cationic polymers may be homopolymers which are cationically substituted or may be formed from two or more types of monomers. The weight average ($M_w$) molecular weight of the polymers will generally be between 100000 and 3 million daltons. The polymers will have cationic nitrogen containing groups such as quaternary ammonium or protonated amino groups, or a mixture thereof. If the molecular weight of the polymer is too low, then the conditioning effect is poor. If too high, then there may be problems of high extensional viscosity leading to stringiness of the composition when it is poured.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give polymers having a cationic charge density in the required range, which is generally from 0.2 to 3.0 meq/gm. The cationic charge density of the polymer is suitably determined via the Kjeldahl method as described in the US Pharmacopoeia under chemical tests for nitrogen determination.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general, secondary and tertiary amines, especially tertiary, are preferred.

Amine substituted vinyl monomers and amines can be polymerised in the amine form and then converted to ammonium by quaternization.

The cationic polymers can comprise mixtures of monomer units derived from amine- and/or quaternary ammonium-substituted monomer and/or compatible spacer monomers.

Suitable (non-limiting examples of) cationic polymers include:
- cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;
- mineral acid salts of amino-alkyl esters of homo- and co-polymers of unsaturated carboxylic acids having from 3 to 5 carbon atoms, (as described in U.S. Pat. No. 4,009,256);
- cationic polyacrylamides (as described in WO95/22311).

Other cationic polymers that can be used include cationic polysaccharide polymers, such as cationic cellulose derivatives, cationic starch derivatives, and cationic guar gum derivatives.

Cationic polysaccharide polymers suitable for use in compositions for use in the invention include monomers of the formula:

A-O—[R—N$^+$(R$^1$)(R$^2$)(R$^3$)X$^-$], wherein: A is an anhydroglucose residual group, such as a starch or cellulose anhydroglucose residual. R is an alkylene, oxyalkylene, polyoxyalkylene, or hydroxyalkylene group, or combination thereof. R$^1$, R$^2$ and R$^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in R$^1$, R$^2$ and R$^3$) is preferably about 20 or less, and X is an anionic counterion.

Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from the Amerchol Corporation, for instance under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581). Examples of such materials include the polymer LR and JR series from Dow, generally referred to in the industry (CTFA) as Polyquaternium 10.

A particularly suitable type of cationic polysaccharide polymer that can be used is a cationic guar gum derivative, such as guar hydroxypropyltrimethylammonium chloride (commercially available from Rhodia in their JAGUAR trademark series). Examples of such materials are JAGUAR C135, JAGUAR C14 and JAGUAR C17.

Mixtures of any of the above cationic polymers may be used.

Cationic polymer will generally be present in a shampoo composition for use in the invention at levels of from 0.01 to 5%, preferably from 0.02 to 1%, more preferably from 0.05 to 0.8% by total weight of cationic polymer based on the total weight of the composition.

Unless otherwise indicated, ratios, percentages, parts, and the like, referred to herein, are by weight.

EXAMPLES

Example 1: Polymer for Use in the Compositions of the Invention

The polymer, designated Polymer P1, for use in the compositions of the invention was prepared in accordance with formula 1. The details are given in Table 1 below.

TABLE 1

Structural Composition of Polymer P1

| Hydrophobe % | Hydrophobe Chain Length (n) when conforming to the structure 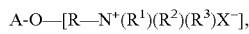 m = 23 | Ethyl Acrylate % | Methacrylic acid % | AMPS % |
|---|---|---|---|---|
| 9 | 12 | 59.5 | 31.5 | 1 |

Polymer P1 Synthesis

A 3 liter, 4 necked round bottom flask equipped with a mechanical stirrer, thermocouple, condenser and nitrogen sparge was charged with 430 g of deionized water and 4.7 g of sodium lauryl sulfate. The flask was then purged with nitrogen and its contents were warmed to 90° C. Then a first initiator solution containing 0.33 g of ammonium persulfate dissolved in 10 g of deionized water was added to the flask. Then a monomer solution was gradually charged to the flask over a period of 107 minutes, wherein the monomer solution contained 633 g deionized water, 18 g of sodium lauryl sulfate and the amounts (as noted in TABLE 1) of each of ethyl acrylate (EA), methacrylic acid (MAA), 2-acrylamido-2-methylpropane sulfonic acid (AMPS) and a lipophilically modified monomer (LIPO) having the following structure:

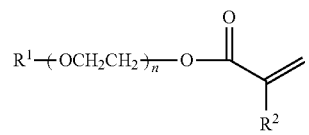

wherein R$^1$ was a linear saturated C$_{12-14}$ alkyl group; R$^2$ is selected from hydrogen or methyl; R$^2$ is selected from hydrogen or methyl, preferably methyl; and n was an average of 20 to 28. Starting simultaneously with the monomer solution charge, a second initiator solution containing 0.33 g of ammonium sulfate in 49 g of deionized water was gradually charged to the flask over a period of 112 minutes. Following the monomer charge and the second initiator solution charge, the transfer lines were rinsed with deionized water followed by a free radical catalyst and activator chase solution. The resulting latex product (Polymer P1) was recovered.

Example 2: Preparation of Antidandruff Shampoo, S1, in Accordance with the Invention and Comparative Antidandruff Shampoos, SA and SB A comparative antidandruff shampoo, designated SA was prepared by the following method:
1. Carbomer was added to water.
2. The Carbomer was then allowed to swell by increasing the pH to pH 5.5-6.5, using a suitable pH modifier.
3. The cleansing surfactants, cationic polymer, antidandruff active, fragrance and preservatives were then added to the swollen polymer and fully dispersed.
4. The resulting formulation was adjusted to the desired pH and viscosity using suitable pH and viscosity modifiers.

Antidandruff shampoos, S1, in accordance with the invention and comparative example SB, were prepared by the following method:
1. Polymer (Polymer P1) was added to water.
2. The polymer was then allowed to swell by increasing the pH, using a suitable pH modifier, until a clear solution was obtained.
3. The cleansing surfactants, cationic polymer, antidandruff active, fragrance and preservatives were then added to the swollen polymer and fully dispersed.
4. The resulting formulation was adjusted to the desired pH and viscosity using suitable pH and viscosity modifiers.

The compositions of Shampoo S1, Comparative Shampoo SA and Comparative Shampoo SB are shown in Table 2 below.

TABLE 2

Compositions of Shampoo S1, in accordance with the invention and Comparative Shampoo SA

| INCI Name | Shampoo SA % w/w | Shampoo SB % w/w | Shampoo S1 % w/w |
|---|---|---|---|
| Water | To 100% | To 100% | To 100% |
| Carbomer (ex. Lubrizol) | 0.6 | 0 | 0 |
| Acrylates Co-Polymer (Carbopol Aqua SF1) | 0 | 0.4 | 0 |
| Polymer 1 | 0 | 0 | 0.4 |
| Sodium Laureth Sulphate | 14 | 14 | 14 |
| Cocamidopropyl Betaine | 1.6 | 1.6 | 1.6 |
| Zinc Pyrithione | 1 | 1 | 1 |
| Fragrance | 0.75 | 0.75 | 0.75 |
| Guar Hydroxypropyltrimonium Chloride | 0.20 | 0.20 | 0.20 |
| Preservatives | 0.9 | 0.9 | 0.9 |
| Viscosity modifiers | 0.6 | 0.36 | 0.8 |
| pH modifiers | 0.4 | 1.26 | 0.11 |
| Dimethicone | 2 | 2 | 2 | pH's were in the range of from 5.5 to 6.5 as measured by calibrated pH meter.

Example 4: Thermal Stability and Degree of Particle Aggregation of Shampoo S1, in Accordance with the Invention and Comparative Shampoos SA and SB Thermal stability and degree of particle aggregation of Shampoo S1, in accordance with the invention and Comparative Shampoos SA and SB were measured using the following procedures:

Thermal stability was tested by placing the shampoo compositions S1, SA and SB in an oven at 45° C. for 12 weeks. The compositions were assessed at frequent intervals over the 12 weeks period for sedimentation of particles.

The degree of particle aggregation was assessed by first diluting the shampoo composition (S1, SA and SB) to a level of 1 in 10 in water. The microstructural appearance of the resulting mixture was captured using an optical microscope at magnification of 20×, using a light polarising filter. Each sample was imaged three times at a consistent exposure. The resulting micrographs were then analysed using ImageJ (an open source and free software for image analysis available at http://imagej.nih.gov/ij/). The micrographs were first converted to a 16-bit image and the visible particles were highlighted using the threshold function at appropriate settings for the analysis. The resulting average particle area was reported in units of $\mu m^2$.

The results are given in Table 3.

TABLE 3

Thermal stability, degree of particle (zinc pyrithione) aggregation and particle size of Shampoo S1, in accordance with the invention and Comparative Shampoo SA

| | Shampoo SA | Shampoo SB | Shampoo S1 |
|---|---|---|---|
| Thermal Stability at 45° C. | >12 weeks | >12 weeks | >12 weeks |
| Degree of particle aggregation Lower = better | High | Very high | Very Low |
| Average Particle Size ($\mu m^2$) determined using ImageJ analysis software | 22 ± 9 | 93 ± 20 | 8 ± 1 |

It will be seen that the degree of particle aggregation of the suspended zinc pyrithione is lower in the shampoo of the present invention than in the comparative shampoos SA and SB, which comprise conventional polymers, resulting in a much smaller particle size. The small particles are deposited more onto the scalp, as seen by Example 5 below.

Example 5: Level of Deposition of Antidandruff Active (Zinc Pyrithione) onto Hair and Scalp; and Log Reduction in *Malassezia Furfur* after Treatment with Shampoo S1, in Accordance with the Invention and Comparative Shampoo SA The amount of antidandruff active deposited onto the hair and scalp (an artificial skin was used to mimic scalp); and the Log reduction in *Malassezia Furfur* treated with Shampoo S1 and Comparative Shampoo SA were measured using the following procedures:

Measurement of Zinc Deposition to Hair

Virgin hair switches were treated with the shampoo of interest. Switches were rinsed and dried before the level of zinc was quantified using x-ray fluorescence (XRF).

Measurement of Zinc Pyrithione Deposition to VIT-ROSKIN®

The treatment of VITROSKIN® consisted of adding 0.2 g of the composition (Shampoo S1 or Comparative Shampoo SA) to the VITROSKIN®, followed by 1.8 ml of water. This was rubbed for 30 s using a teflon rod and the solution was then removed. The surface was then rinsed by adding 4 ml of sterile water to the VITROSKIN®, rubbing for 30 s using a teflon rod and then removing the solution. The rinsing step was repeated one more time.

Following the treatment, zinc pyrithione was extracted from the VITROSKIN® into methanol before a DPS (2,2'-dipyridyl disulphide) derivation was conducted. The zinc pyrithione level in the resulting liquor was then quantified using a Waters ACQUITYUPLC System coupled to UV detector at an absorption wavelength of 235 nm.

Measurement of In-Vitro Log Reduction *Malassezia Furfur*

*Malassezia furfur* 7019 in Pityrosporum Broth (comprising 10 g Bacteriological Peptone, 0.1 g Yeast extract, 10 g Ox-bile, 2.5 g Taurocholic acid, 10 g Glucose, 1 L Deionised water, 0.5 ml Tween 60, 1 ml Glycerol and 0.5 ml UHT milk; adjusted to pH 6.2) was grown for 2 days and adjusted to a final concentration of $2-6 \times 10^5$ cells/ml. 0.2 ml of the above *Malassezia* was pipetted out onto VITROSKIN® (10.34 $cm^2$) and left for 30 minutes. The treatment of VITROSKIN® consisted of adding 0.2 g of the composition (Shampoo S1 or Comparative Shampoo SA) to the VITROSKIN®, followed by 1.8 ml of water. This was rubbed for 30 s using a teflon rod and the solution was then removed. The surface was then rinsed by adding 4 ml of sterile water to the VITROSKIN®, rubbing for 30 s using a teflon rod and removing the solution. The rinsing step was repeated one more time.

For the measurement of Log reduction of *Malassezia furfur*, treated VITROSKIN® was first placed onto a Modified Dixon Agar Plate and incubated at 32° C. for 24 h. Following incubation, each piece of VITROSKIN® was cut off and placed into a vial containing 10 ml of PBS buffer (pH 7.2), 0.1% Triton X-100 and 0.5% Tween-80. The vial containing VITROSKIN® was vortexed for 1 minute. 20 μl of $10^0$-$10^{-3}$ dilutions were plated onto Modified Dixon Agar Plates, and incubated at 32° C. for 3-4 days. The number of colonies on each plate were then counted, and final numbers determined by multiplying by the appropriate dilution. The Log reduction of *Malassezia furfur* was then calculated from the measurements.

Each sample was run in triplicate and was tested three times.

The results are presented in Table 4.

TABLE 4

Level of deposition of Zinc Pyrithione onto hair and scalp; and Log reduction in *Malassezia Furfur* after treatment with Shampoo S1, in accordance with the invention and Comparative Shampoo SA

| Test | SA | S1 |
| --- | --- | --- |
| Zinc Pyrithione Deposition to Hair (ppm) (+/−standard deviation) Higher = better | 1121 ± 246 | 310 ± 63 |
| Zn from Zinc Pyrithione Deposition to Vitro Skin (μg/$cm^2$) (+/−standard error) Higher = better | 0.19 ± 0.03 | 0.29 ± 0.03 |
| Log Reduction (*Malassezia Furfur*) (+/−standard error) Lower = better | −1.12 ± 0.07 | −1.63 ± 0.07 |

It will be seen that the antidandruff active is selectively deposited onto scalp rather than hair when the shampoo of the present invention (S1) is used. This is advantageous because the bioavailability of the antidandruff agent is consequentially increased on the scalp. Further, lower deposition of Zinc Pyrithione onto the hair gives better hair feel, in line with consumer preference. Additionally, the zinc pyrithione is highly disaggregated when used in the shampoo of the present invention (Table 3). This results in a significant reduction in the level of *Malassezia Furfur* on VITROSKIN® versus the highly aggregated zinc pyrithione in the carbomer structured shampoo (SA).

The invention claimed is:

1. An aqueous anti-dandruff shampoo composition which comprises:
    (I) 2-40 wt % of a cleansing surfactant selected from the group consisting of sodium lauryl sulphate, sodium lauryl ether sulphate, sodium lauryl ether sulphosuccinate, ammonium lauryl sulphate, ammonium lauryl ether sulphate, sodium cocoyl isethionate and lauryl ether carboxylic acid, coco betaine, cocamidopropyl betaine, sodium cocoamphoacetate and mixtures thereof,
    (II) 0.01 to 30 wt % suspended particles of an anti-dandruff agent that is zinc pyrithione,
    (III) 0.05 to 4 wt % an anti-settling, thickening polymer, wherein the anti-settling, thickening polymer, comprises:
        (a) 50 to 65 wt % of structural units ethyl acrylate;
        (b) 25 to 40 wt % of structural units of methacrylic acid;
        (c) 0.75 to 2.0 wt % of structural units of 2-acrylamido-2-methylpropane sulfonic acid;
        (d) 7.5 to 9 wt % of structural units of a specialized associated monomer having the following structure

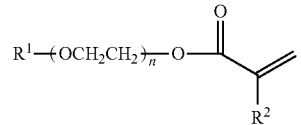

wherein $R^1$ is a linear saturated $C_{12-14}$ alkyl group; wherein $R^2$ is a methyl group; and wherein n is an average of 20 to 28; and wherein the sum of the weight percentages of structural units (a)-(d) is equal to 100 wt % of the anti-settling, thickening polymer.

2. The aqueous anti-dandruff shampoo composition as claimed in claim 1, which further comprises an insoluble conditioning silicone.

3. The aqueous anti-dandruff shampoo composition as claimed in claim 1, which has a pH of 3 to 7.

4. The aqueous anti-dandruff shampoo composition as claimed in claim 1, which further comprises an additional antidandruff agent that is soluble in the aqueous formulation at 15 to 25° C.

5. The aqueous anti-dandruff shampoo composition as claimed in claim 1, which further comprises a fragrance.

6. A method of treating hair comprising applying to the hair, the aqueous anti-dandruff shampoo composition of claim 1.

7. A method as claimed in claim 6, further comprising rinsing the hair with water.

* * * * *